United States Patent [19]

Beede et al.

[11] 4,082,705

[45] Apr. 4, 1978

[54] PRESSURE SENSITIVE ADHESIVE COMPOSITIONS

[75] Inventors: Charles H. Beede; Theodore Blumig, both of East Brunswick, N.J.

[73] Assignee: Johnson & Johnson, New Brunswick, N.J.

[21] Appl. No.: 655,602

[22] Filed: Feb. 5, 1976

[51] Int. Cl.$^2$ .................... C08L 33/08; C08L 23/20; C08L 9/00

[52] U.S. Cl. .................. 260/4 R; 260/876 B; 260/887; 260/897 B; 260/901; 526/291; 526/312; 427/207 B

[58] Field of Search ............... 260/4 R, 876 B, 897 B, 260/887, 901; 526/291, 312; 427/207 B

[56] References Cited

U.S. PATENT DOCUMENTS

| | | | |
|---|---|---|---|
| 2,808,349 | 10/1957 | Melamed | 529/291 |
| 3,321,451 | 5/1967 | Gander | 526/312 |
| 3,497,550 | 2/1970 | Samour | 526/312 |
| 3,861,948 | 1/1975 | Samour et al. | 526/312 |
| 3,901,857 | 8/1975 | Sackman et al. | 526/312 |
| 3,934,595 | 1/1976 | Dermain | 526/312 |
| 3,972,328 | 8/1976 | Chen | 128/156 |

*Primary Examiner*—John C. Bleutge

[57] ABSTRACT

Surgical pressure sensitive adhesive compositions having improved long term skin adhesion characteristics comprising a polyacrylate, rubber, or polyolefin pressure sensitive adhesive and a cross-linked hydrophilic random interpolymer. The interpolymer comprises an ester of an $\alpha,\beta$-olefinically unsaturated carboxylic acid and an alcohol having a quaternary ammonium group; an $\alpha,\beta$-olefinically unsaturated comonomer; and a difunctional cross-linking monomer. The adhesive compositions are useful in surgical adhesive tapes, adhesive bandages, and like items comprising a pressure sensitive adhesive.

8 Claims, No Drawings

PRESSURE SENSITIVE ADHESIVE COMPOSITIONS

This invention relates to improved surgical pressure sensitive adhesive compositions and to methods of making the same. More particularly, this invention relates to pressure sensitive adhesive compositions which comprise cross-linked hydrophilic random interpolymers and which have improved adhesion, especially to the human skin.

This invention also relates to surgical adhesive tapes and to adhesive bandages and dressings, such as coverings for cuts, abrasions, and the like, which comprise a flexible backing member one of whose major surfaces has adhered thereto a coating of a pressure sensitive adhesive composition containing a cross-linked hydrophilic polymer.

Several types of pressure sensitive adhesives are known to be useful as the adhesive component in adhesive bandages, self-adherent surgical drapes and the like. Acrylate pressure sensitive adhesives, that is, pressure sensitive adhesives comprising random interpolymers derived from at least 50% by weight of an alkyl acrylate wherein the alkyl group has from 4 to about 12 carbons, are well known for their hypoallergenic nature and good cohesive strength. However, pressure sensitive adhesives comprising acrylate polymers sometimes suffer from the disadvantage that adhesion to human skin is poor under hot, humid conditions such as would occur if the wearer were sweating after vigorous exercise.

Another class of polymers that have been proposed for use as pressure sensitive adhesives are the polyolefins derived from monomers having from about 6 to about 11 carbons. Representative examples of polyolefins which are useful in pressure sensitive adhesives for surgical or medical use are poly(1-heptene), poly(1-octent), and poly(1-decene). Such polymers are advantageous in that they are essentially single component adhesives, have reduced tendency to generate allergic reactions, and possess good cohesive strength characteristics. The polyolefins, however, have not enjoyed wide acceptance as pressure sensitive adhesives because they are relatively expensive and are impermeable to moisture.

A third class of polymers which has been suggested for use in pressure sensitive adhesives is the compounded systems based on natural or synthetic rubber polymers. Representatives of this class of polymers include poly(cisisoprene), poly(butadienestyrene), and block copolymers of butadiene or isoprene. Rubber-based pressure sensitive adhesives are relatively inexpensive and generally possess acceptable tack and cohesion characteristics. These adhesives, however, suffer from the disadvantage that they involve many components (e.g., tackifiers, antioxidants, etc.) and frequently are the source of allergic reactions. In addition, they are relatively moisture impermeable and frequently are deficient in the necessary long-term skin adhesion characteristics.

A pressure-sensitive adhesive must have certain characteristics to be useful. It must be sufficiently tacky, i.e., have sufficient "grab" or quick-stick, to wet and adhere quickly to the surface to which it is to be adhered. It must also continue to adhere to that surface over extended periods of time. The adhesive must also have sufficient internal strength to prevent its splitting and leaving particles of adhesive on a surface to which an article coated with the adhesive has been adhered when the article is removed. Where the pressure-sensitive adhesive is designed for application to the skin, the problems of adherence are substantially increased. Although the initial tack or stick may be good, adherence over an extended period of time for many pressure-sensitive adhesives is found to be relatively poor whether because of movement of the underlying skin or the nature of the underlying skin surface as where perspiration and other surface changes may occur. The problem is further complicated by the fact that any pressure-sensitive adhesive designed for application to the skin must release from the skin sufficiently readily to permit removal without skin damage. Where the adhesive is too strongly adhered to the skin and has substantial internal strength, small particles of the upper layer of skin are removed with the adhesive with resulting irritation. As a result, although many pressure-sensitive adhesives are available for various commercial uses, relatively few have been found which are suitable for skin application.

In accordance with the present invention, surgical pressure sensitive adhesive compositions having excellent long-term skin adhesion characteristics are provided which comprise from about 82 to about 97½ parts by weight of a pressure sensitive adhesive and, correspondingly, from about 18 to about 2½ parts by weight of a non-tacky, cross-linked, hydrophilic random interpolymer which can absorb significant amounts (for example, from about 10 to about 125 its own weight) of water. Non-tacky, cross-linked, random hydrophilic interpolymers which have been found to improve the long-term skin adhesion of polyacrylate, rubber and polyolefin pressure sensitive adhesives and which are useful in the practice of the present invention are derived from the polymerization of a mixture of monomers comprising an ester of an $\alpha,\beta$-olefinically unsaturated carboxylic acid and a monohydric or polyhydric alcohol having a terminal quaternary ammonium group; an $\alpha,\beta$-olefinically unsaturated comonomer; and a cross-linking agent comprising a difunctional monomer derived from an $\alpha,\beta$-olefinically unsaturated carboxylic acid. Methods for preparing such polymers are disclosed in U.S. patent application Ser. NO. 509,207 filed Sept. 25, 1974, now abandoned, and replaced by continuation application Ser. No. 674,471, which application, and the teachings therein, are hereby incorporated herein by reference.

As used herein, the term "long term skin adhesion" refers to the degree of adherence of the pressure sensitive adhesive mass to the human skin at 24 hours after application thereof. The long term skin adhesion of a particular adhesive mass may be determined in accordance with the following test. 1×3 inches tapes comprising a suitable backing material coated with the adhesive to be tested are placed on the upper arm of a number of human subjects and left there for 24 hours, during which time the subjects pursue their normal activities. At the end of the test period the tapes are checked for skin adherence and rated on a scale of from 0 to 100. Where essentially no separation of tape from the skin, such as lifting of corners or other partial removal, has occurred, the long term skin adhesion is given a rating of 100 (perfect adhesion). Where the tape has completely separated from the skin of the test subject, the long term skin adhesion is rated as 0 (complete failure). Intermediate degrees of adhesion are assigned values between 0 to 100, with higher values being indicative of better adhesion characteristics. Each adhesive coated tape is tested on a number of subjects (usually 24) and the individual test results are averaged to give the final score.

DESCRIPTION OF THE PREFERRED EMBODIMENTS

There has now been discovered a pressure sensitive adhesive composition having improved long term skin adhesion characteristics comprising from about 82 to about 97 ½ parts by weight of a pressure sensitive adhesive polymer and, correspondingly, from about 18 to about 2½ parts by weight of a non-tacky, hydrophilic, random interpolymer comprising: (A) from about 10 parts by weight to about 90 parts by weight of an ester of an $\alpha,\beta$-olefinically unsaturated carboxylic acid and a monohydric or polyhydric alcohol having a terminal quaternary ammonium group, and (B) correspondingly, from about 90 parts by weight to about 10 parts by weight of at least one $\alpha,\beta$-olefinically unsaturated comonomer, and (C) at least 0.02 parts by weight of a cross-linking agent comprising a difunctional monomer derived from an $\alpha,\beta$-olefinically unsaturated carboxylic acid; said $\alpha,\beta$-olefinically unsaturated comonomer (B) comprising (a) at least 10% by weight of the total weight of monomers (A) and (B) of an acid comonomer, or (b) at least 20% by weight of the total weight of monomers (A) and (B) of an amide comonomer, or (c) at least 10% by weight of the total weight of monomers (A) and (B) of a combination of acid and amide comonomers, said combination containing at least 5% by weight of the total weight of monomers (A) and (B) of an acid monomer.

Pressure sensitive adhesive polymers whose long term skin adhesion qualities may be improved through the practice of the present invention include acrylate pressure sensitive adhesives (as hereinbefore defined), rubber-based pressure sensitive adhesives, and polyolefin-based pressure sensitive adhesives.

The monomeric ethylenically unsaturated esters useful in the preparation of the aforementioned cross-linked hydrophilic random interpolymers include esters of an $\alpha,\beta$-olefinically unsaturated carboxylic acid and a monohydric or polyhydric alcohol having a terminal quaternary ammonium group. Such monomeric esters have a structure represented by the general formula:

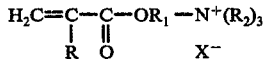

wherein R is selected from the group consisting of hydrogen and $C_1$ to $C_4$ alkyl; $R_1$ is selected from the group consisting of $C_1$ to $C_4$ alkylene and hydroxy substituted $C_1$ to $C_4$ alkylene; each $R_2$ is selected from the group consisting of $C_1$ to $C_4$ alkyl; and $X^-$ is an anion, for example $Cl^-$, $Br^-$, $I^-$, and $CH_3SO_4^-$, sufficiently acidic to form a salt with amino nitrogen. Such esters are exemplified by 2-methacryloyl-oxyethyltrimethylammonium methyl sulfate and 2-hydroxy-3-methacryloyloxypropyltrimethylammonium chloride, the latter being preferred.

The difunctional cross-linking monomers useful in the preparation of the cross-linked hydrophilic polymer include the esters and amides of $\alpha,\beta$-olefinically unsaturated acids selected from the group consisting of the compounds defined by structural formulas I, II and III below:

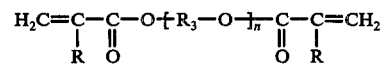

wherein R is hydrogen or $C_1$ to $C_4$ alkyl; $R_3$ is $C_1$ to $C_6$ alkylene; and n is an integer from 1 to 3;

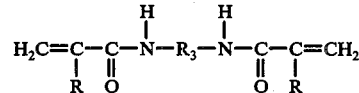

wherein R is hydrogen or $C_1$ to $C_4$ alkyl; and $R_3$ is $C_1$ to $C_6$ alkylene; and

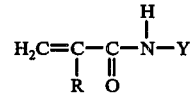

wherein R is hydrogen or $C_1$ to $C_4$ alkyl; and Y is selected from the group consisting of

and

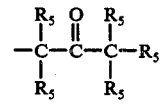

wherein $R_4$ is selected from the group consisting of hydrogen and $C_1$ to $C_5$ alkyl; and each $R_5$ is selected from the group consisting of hydrogen and $-CH_2OH$, provided, however, that at least one $R_5$ is $-CH_2OH$.

Examples of useful difunctional monomers include ethylene glycol dimethacrylate and diacrylate, diethyleneglycol dimethacrylate and diacrylate, triethyleneglycol dimethacrylate and diacrylate, 1,3-propanediol dimethacrylate and diacrylate, 2,2-dimethylpropanediol diacrylate, tripropylene glycol dimethacrylate and diacrylate, 1,3-butylene glycol dimethacrylate and diacrylate, N,N'-propylenebisacrylamide, N,N'-methylenebisacrylamide; N-1-alkylol amides of $\alpha,\beta$-olefinically unsaturated carboxylic acid, which amides have from 4 to 8 carbon atoms, exemplified by N-1-methanol acrylamide, N-1-ethanolacrylamide, N-1-propanolacrylamide, N-methanolmethacrylamide, N-1-ethanolmethacrylamide and hydroxymethyl diacetone acrylamide (available from Lubrizol Corporation). The preferred difunctional monomer is N,N'-methylenebisacrylamide.

Olefinically unsaturated comonomers that may be used in preparing the cross-linked, hydrophilic random interpolymers include $\alpha,\beta$-olefinically unsaturated monomers such as the vinyl monomers, as well as $\alpha,\beta$-olefinically unsaturated carboxylic acids of from 3 to 6 carbon atoms and the lower alkyl esters and amides thereof, 2-($C_1$–$C_4$) alkyl substituted acrylic and crotonic acids and esters and amides thereof, and N-substituted amides of the above acids. Examples of such $\alpha,\beta$-olefinically unsaturated monomers include sodium vinyl sulfate, vinyl acetate, methyl vinyl ether, crotonic acid, crotonamide, acrylic acid, methyl acrylate, methyl crotonate, ethyl acrylate, ethyl crotonate, methacrylic acid, 2-ethylacrylic acid, 2-methylcrotonic acid, butyl methacrylate, ethyl methacrylate, ethyl 2-methylcrotonate, acrylamide, methacrylamide, 2-ethylcrotonamide, 2-ethyl-acrylamide, N-isopropyl acrylamide, diacetone acrylamide, N-t-butyl acrylamide, N-2-ethanol acrylamide, N-3-propanol acrylamide and N-methyl methacrylamide. Of these, the preferred comonomers are acrylic acid, methacrylic acid, acrylamide and methacrylamide.

Preferably the hydrophilic cross-linked random interpolymer is made from a mixture of monomers comprising from about 10 to about 80% by weight of said mixture of said α,β-olefinically unsaturated ester of a carboxylic acid and a monohydric or polyhydric alcohol having a terminal quaternary ammonium group; and at least about 20% by weight of said mixture of an α,β-olefinically unsaturated comonomer, from about 5 to about 35% by weight of the mixture (total monomers—excluding the crosslinking agent) comprising a comonomer selected from the group consisting of acrylic acid and methacrylic acid (acrylic acid being most preferred), and from about 10 to about 85% by weight of the mixture comprising acrylamide or methacrylamide (acrylamide being most preferred). Clearly the total amount of the monomers in said mixture will be 100% and therefore if an amount equal to or approaching the maximum of one particular monomer is employed, then the relative amounts of the remaining monomers must be reduced accordingly. The amount of difunctional monomer cross-linking agent employed in this preferred embodiment is from about 0.2 to about 5%, based on the weight of the mixture, from about 0.05 to about 1% being particularly preferred.

The following examples are given for purposes of illustratng the preparation and use of the improved pressure sensitive adhesive compositions of the present invention which is not to be construed as being limited thereto.

EXAMPLE I

This Example shows the preparation of a cross-linked, hydrophilic random interpolymer comprising 45 parts by weight 2-hydroxy-3-methacryloyloxypropyl trimethylammonium chloride, 10 parts by weight acrylic acid, 45 parts by weight acrylamide, and 0.05 parts by weight N,N'-methylenebisacrylamide.

A 5-liter multi-neck flask, equipped with a nitrogen inlet, mechanical stirrer, thermometer, reflux condenser and an addition funnel was charged with the following reagents:

| | |
|---|---|
| 2-hydroxy-3-methacryloyloxypropyl trimethylammonium chloride (commercially available from Alcolac Chem. Corp. as Sipomer* Q-1) | 108g. |
| Acrylic acid | 24g. |
| Acrylamide | 108g. |
| N,N'-methylenebisacrylamide | 0.12g |
| Water | 2700g. |

2-hydroxy-3-methacryloyloxypropyl trimethylammonium chloride has the structure

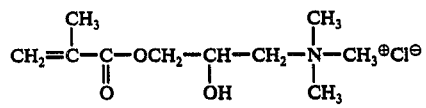

The structure of acrylic acid is $CH_2=CH-COOH$, the structure of acrylamide is

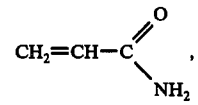

and the structure of N,N'-methylenebisacrylamide is

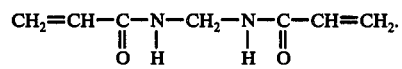

After purging the system with nitrogen for 100 minutes, the contents were heated until the temperature reached 55° C. Then a solution of 2.4 grams of ammonium persulfate in 10 ml. of water was added. When the temperature reached 68°, and the viscosity of the reaction mixture became such that the stirrer began to labor, 240.0g. of methanol were added over a 10 min. period and the reaction mixture cooled. The colloidal dispersion obtained had a solids content of 7.76%, equivalent to 100% conversion.

The polymer was obtained as a brittle film by drying down the dispersion at 100° C. The dried polymer was charged into a ball mill and pulverized. The material was sieved to obtain material less than 244 microns in diameter.

EXAMPLE II

A rubber based pressure sensitive adhesive having the following composition is prepared according to well-known techniques:

| | |
|---|---|
| Pale crepe rubber | 31.3 |
| Zinc oxide | 9.7 |
| Corn starch | 4.7 |
| Lanolin | 9.6 |
| Titanium dioxide | 2.3 |
| Aluminum Hydrate H710 (Alcoa Co.) | 12.1 |
| Water | 0.7 |
| Tackifier (mixture of rosin acids commercially available from Hercules as NC-11) | 28.2 |
| Dibutyldithio zinc carbamate | 1.4 |

EXAMPLE III

Solutions of acrylate pressure sensitive adhesive polymers having the compositions given below were prepared.

| | A | B |
|---|---|---|
| 2-Ethylhexyl Acrylate | 60 | 60 |
| Vinyl Acetate | 25 | 25 |
| t-Butylacrylamide | — | 15 |
| Diacetoneacrylamide | 15 | — |
| Silane | 0.05 | 0.035 |
| Cyclohexane | 150 | — |
| Ethyl Acetate | — | 150 |
| Williams Plasticity, mm | 2.8–3.2 | 2.25 |
| % Solids | 40 | 40 |

Reaction mixtures were prepared by mixing the indicated monomers and solvent in a polymerization flask and adding thereto 0.02 grams/100 grams of monomer of benzoyl peroxide. The reaction mixture was heated to reflux and maintained there for 6 hours. The resulting polymer solution was cooled to room temperature after which the solids content of the solutions and Williams plasticity of the polymers were determined in accordance with standard techniques.

EXAMPLE IV

Four pressure sensitive adhesive solutions having the compositions set forth in the left hand portion of Table I were prepared in accordance with the following general procedure. The designated amount of the crosslinked, hydrophilic random interpolymer of Example I was wetted with 10 ml. of cyclohexane and added to the designated amount of the various polyacrylate pressure sensitive adhesive solutions of Example III. To this mixture was then added 0.5 g of dibutyltin dioctoate (an organic catalyst) predissolved in 2.0 ml. of cyclohexane. The entire mixture was then stirred until homogeneous.

Adhesive sheets were then prepared by bar coating the pressure sensitive adhesive solutions IVA through IVD on either 180 × 54 rayon acetate tafetta or one-sixteenth inches thick polyester urethane foam backing. The clearance on the bar coater was set at 12 mils. The coated backing was dried in a steam heated cabinet for 1.5 hours, and thereafter cured for 2.0 minutes at 170° C in a forced air oven. The weight of the adhesive mass thus applied was about 3 ounces/yd.$^2$. The pressure sensitive adhesive coated samples were cut into 1×3 inch strips and tested for their long term skin adhesion properties. Control samples (without the hydrophilic random interpolymer of Example I) were prepared and tested simultaneously.

the manner recited in Example IV. The amount of adhesive on the coated strips was about 2 ounces/yd$^2$. The ratio of the polyolefin component to the hydrophilic random interpolymer component in the final adhesive was 91:9.

The test results showed that the adhesive strip had a long term skin adhesion of 88; a control strip (i.e., polyoctene without the polymer of Example I) had a long term skin adhesion of 84. It is seen that the addition of the aforedescribed random hydrophilic interpolymer to the polyolefin pressure sensitive adhesive gives improved long term skin adhesion.

EXAMPLE VI

A rubber type pressure sensitive adhesive modified with the polymer of Example I was prepared as follows. 9 grams of the polymer of Example I was added to 91 grams of the rubber-based pressure sensitive adhesive of Example II. These components were mixed on a standard rubber mill for about 10 minutes. The resulting adhesive was applied to 80 × 56 cotton backing having a weight of 3 ounces/yd$^2$. The amount of adhesive on the coated cotton was about 4.5 ounces/yd$^2$. The adhesive coated samples were tested as hereinbefore described and found to have a long term skin adhesion value of 90. The control without the polymer of Example I had a long term skin adhesion value of 80. The addition of the random hydrophilic interpolymer to the rubber type pressure sensitive adhesive gives improved

TABLE I

| Sample No. | Example III A | | Example III B | | grams of Polymer Example I* | Weight Ratio Example III Polymer Example I Polymer | Williams Plasticity, Final Adhesive |
|---|---|---|---|---|---|---|---|
| | grams solution at 40% solids | grams dry polymer | grams solution at 40% solids | grams dry polymer | | | |
| IV A | 225.0 | 90.0 | — | — | 10.0 | 90/10 | 2.95 |
| IV B | — | — | 225.0 | 90.0 | 10.0 | 90/10 | 2.26 |
| IV C | — | — | 100.0 | 40.0 | 7.5 | 84/16 | N.D. |
| IV D | — | — | 100.0 | 40.0 | 3.5 | 92/8 | N.D. |

All samples contain 0.5 grams of Dibutyl tin dioctoate dissolved in 2.0 ml cyclohexane
N.D. = not determined
*Wetted with 10 ml. of cyclohexane

TABLE II

| Sample No. | Backing Material | Long Term Skin Adhesion | |
|---|---|---|---|
| | | Adhesive of Invention | Control |
| IV A | rayon acetate | 83 | 78 |
| IV B | rayon acetate taffeta | 84 | 79 |
| IV C | polyester urethane foam | 98 | 88 |
| IV D | rayon acetate taffeta | 81,82 $^{1)}$ | 78.72 $^{1)}$ |

$^{1)}$ duplicate determinations

The results of the long term skin adhesion tests are reported in the right hand portion of Table II. These results clearly demonstrate that the addition of the random hydrophilic interpolymer improve the long term skin adhesion characteristics of polyacrylate pressure sensitive adhesives.

EXAMPLE V

A polyolefin pressure sensitive adhesive modified with the polymer of Example I was prepared as follows. 9.0 g of the random interpolymer of Example I was added to 227.5 of a 40% solids solution in heptane of poly(1-octene) and mixed until homogeneous. The poly(1-octene) was prepared in accordance with Example I-B of U.S. Pat. No. 3,635,755. The resulting pressure sensitive adhesive solution was applied to 180 × 54 rayon acetate tafetta, dried, cut into strips and tested in long term skin adhesion.

While several specific embodiments of the invention have been particularly described, they are provided by way of illustration, and it will be appreciated that many variations and modifications thereof may be made without departing from the spirit and scope of the invention.

What is claimed is:

1. An improved pressure sensitive adhesive composition comprising from about 82 to about 97.5 parts by weight of a pressure sensitive adhesive polymer and, correspondingly, from about 2.5 to about 18 parts by weight of a non-tacky, cross-linked, hydrophilic random interpolymer, said interpolymer comprising:
   (A) from about 10 to about 90 parts by weight of a monomeric ester of an $\alpha,\beta$-olefinically unsaturated carboxylic acid and a monohydric or polyhydric alcohol having a terminal quaternary ammonium group, said ester having the structure:

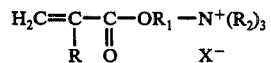

wherein R is selected from the group consisting of hydrogen and $C_1$ to $C_4$ alkyl; $R_1$ is selected from the group consisting of $C_1$ to $C_4$ alkylene and hydroxy substituted $C_1$ to $C_4$ alkylene; each $R_4$ is selected from the group consisting of $C_1$ to $C_4$ alkyl; and $X^-$ is an anion sufficiently acidic to form a salt with amino nitrogen;

(B) correspondingly, from about 90 to about 10 parts by weight of an $\alpha,\beta$-olefinically unsaturated comonomer; and (C) at least 0.02 part by weight of a cross-linking agent comprising a difunctional monomer selected from the esters and amides of $\alpha,\beta$-olefinically unsaturated acids selected from the group consisting of the compounds defined by structural formulas I, II and III below:

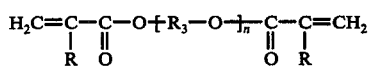   I wherein R is hydrogen or $C_1$ to $C_4$ alkyl; $R_3$ is $C_1$ to $C_6$ alkylene; and $n$ is an integer from 1 to 3;

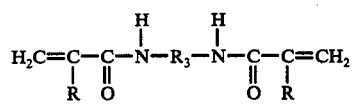   II wherein R is hydrogen or $C_1$ to $C_4$ alkyl; and $R_3$ is $C_1$ to $C_6$ alkylene; and

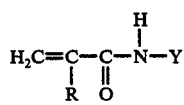   III wherein R is hydrogen or $C_1$ to $C_4$ alkyl; and Y is selected from the group consisting of

and

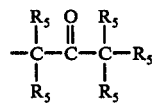

wherein $R_4$ is selected from the group consisting of hydrogen and $C_1$ to $C_5$ alkyl; and each $R_5$ is selected from the group consisting of hydrogen and —CH$_2$OH; provided, however, that at least one $R_5$ is —CH$_2$OH;

said comonomer comprising (a) at least 10% by weight of the total weight of monomers (A) and (B) of an acid comonomer or (b) at least 20% by weight of the total weight of monomers (A) and (B) of an amide comonomer, or (C) at least 10% by weight of the total weight of monomers (A) and (B) of a combination of acid and amide comonomers, said combination containing at least 5% by weight of the total weight of monomers (A) and (B) of an acid comonomer.

2. A pressure sensitive adhesive composition according to claim 1 wherein said ester of an $\alpha,\beta$-olefinically unsaturated acid and a monohydric or polyhydric alcohol having a terminal quaternary ammonium group is selected from the group consisting of 2-methacryloyloxyethyltrimethylammonium chloride and 2-hydroxy-3-methacryloyloxypropyltrimethylammonium chloride.

3. A pressure sensitive adhesive composition according to claim 1 wherein said crosslinking agent is N,N'-methylenebisacrylamide.

4. A pressure sensitive adhesive composition according to claim 1 wherein said acid comonomer is selected from the group consisting of acrylic acid and methacrylic acid and said amide comonomer is selected from the group consisting of acrylamide and methacrylamide.

5. A pressure sensitive adhesive composition according to claim 1 wherein said pressure sensitive adhesive is selected from the group consisting of acrylate pressure sensitive adhesives, rubber based pressure sensitive adhesives, and polyolefin pressure sensitive adhesives.

6. A pressure sensitive adhesive composition according to claim 1 wherein said interpolymer comprises from about 10 to about 80 parts by weight of said ester of an $\alpha,\beta$-olefinically unsaturated carboxylic acid and a monohydric or polyhydric alcohol having a terminal quaternary ammonium group and at least about 20 parts by weight of an $\alpha,\beta$-olefinically unsaturated comonomer.

7. A pressure sensitive adhesive composition according to claim 1 wherein said ester of an $\alpha,\beta$-olefinically unsaturated carboxylic acid and a monohydric or polyhydric alcohol having a quaternary ammonium group is 2-hydroxy-3-methacryloyloxypropyltrimethylammonium chloride; said acid comonomer is acrylic acid; and said amide comonomer is acrylamide.

8. A pressure sensitive adhesive composition according to claim 1 wherein $X^-$ is selected from the group consisting of $Cl^-$, $Br^-$, $I^-$ and $CH_3SO_4^-$.

* * * * *

UNITED STATES PATENT AND TRADEMARK OFFICE
CERTIFICATE OF CORRECTION

PATENT NO. : 4,082,705
DATED : April 4,1978
INVENTOR(S) : Charles H. Beede, et al.

It is certified that error appears in the above-identified patent and that said Letters Patent are hereby corrected as shown below:

```
Column 1, Line 39, "poly(1-octent)" should be
          -- poly(1-octene) --.
Column 5, Line 32, "about 0.2" should be -- about 0.02 --.
Column 7, Table 2, under "Backing Material", "rayon
          acetate" should be -- rayon acetate taffeta --.
Column 7, Table 2, under "Control," "78.72$^{1)}$" should be
          -- 78,72$^{1)}$ --.
Column 8, Line 68, "each $R_4$" should be -- each $R_2$ --.
Column 10, Line 7, "or (C)" should be -- or (c) --.
```

Signed and Sealed this

Twenty-first Day of November 1978

[SEAL]

Attest:

RUTH C. MASON
Attesting Officer

DONALD W. BANNER
Commissioner of Patents and Trademarks